United States Patent [19]

Fukuhara

[11] 4,175,447

[45] Nov. 27, 1979

[54] APPARATUS FOR DETECTING CRACK LENGTH OF A TEST PIECE IN A FATIGUE TEST

[75] Inventor: Toshihiko Fukuhara, Hatano, Japan

[73] Assignee: Kabushiki Kaisha Komatsu Seisakusho, Tokyo, Japan

[21] Appl. No.: 954,600

[22] Filed: Oct. 25, 1978

[30] Foreign Application Priority Data

Oct. 26, 1977 [JP]  Japan ............................... 52-127640

[51] Int. Cl.² ............................................ G01N 3/32
[52] U.S. Cl. ..................................... 73/799; 73/808
[58] Field of Search .................. 73/799, 808, 810, 811, 73/826

[56] References Cited

U.S. PATENT DOCUMENTS

| 3,918,299 | 11/1975 | Donnadieu | 73/799 X |
| 3,983,745 | 10/1976 | Juusola | 73/799 X |

*Primary Examiner*—Jerry W. Myracle

*Attorney, Agent, or Firm*—Armstrong, Nikaido, Marmelstein & Kubovcik

[57] ABSTRACT

An apparatus for detecting crack length of a test piece in a fatigue test wherein crack length is automatically detected and the tip of the crack is displayed on a monitor.

A test piece having a crack thereon is irradiated by a Strobo light through an optical-scope. Reflected beams from the test piece are focused on a camera tube by passing through the optical-scope thereby forming an image of the crack on the camera tube.

The image is then picked up by a scan converter memory so as to be memorized for an extended period.

The memorized image is then introduced into an image analyser while monitored on a monitor screen. The tip of the crack is analysed and calculated in the image analyser and the position of the optical-scope is adjusted accordingly.

A command controller is employed to control an overall time sequence of the entire apparatus.

10 Claims, 8 Drawing Figures

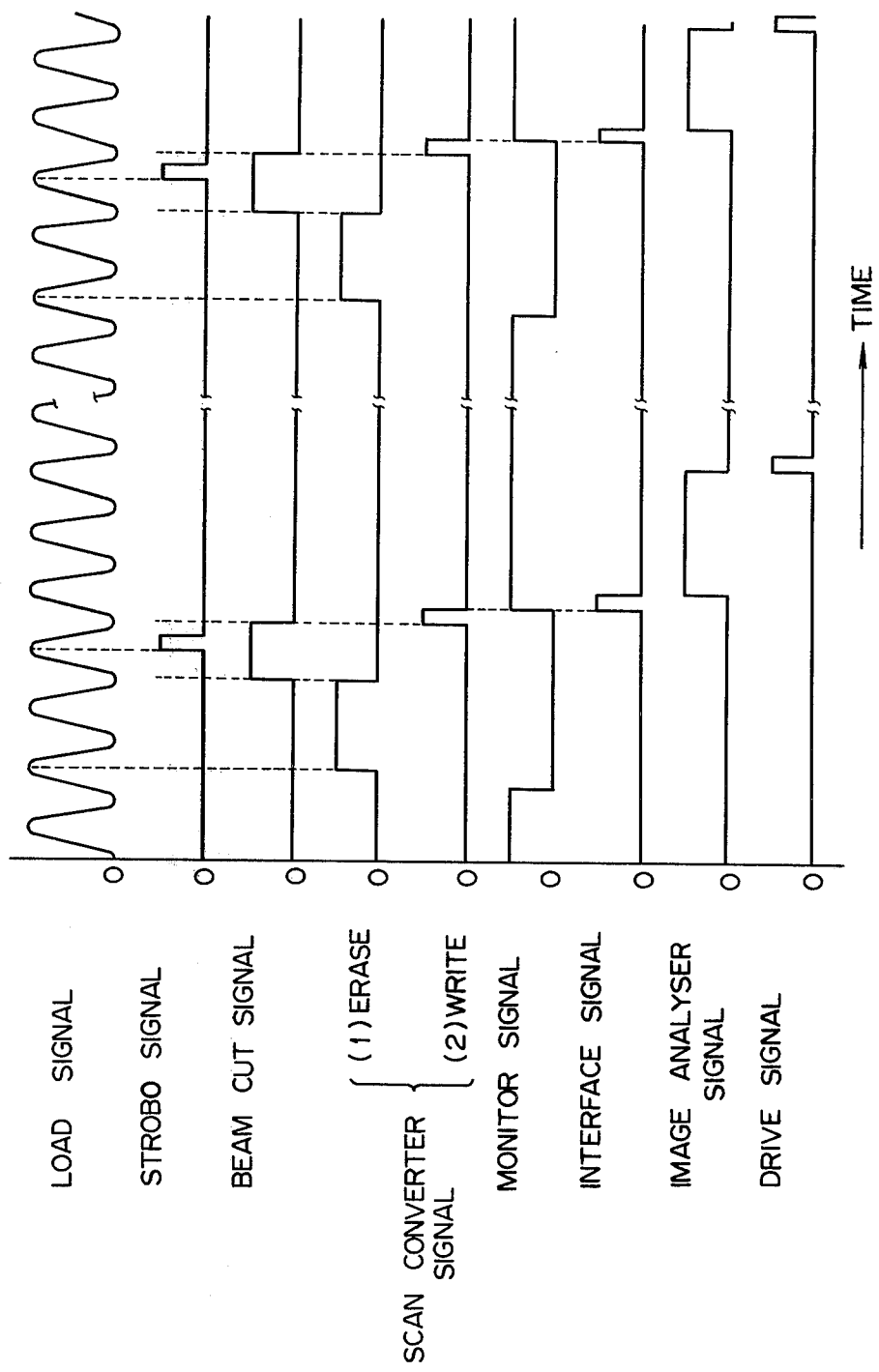

APPARATUS FOR DETECTING CRACK LENGTH OF A TEST PIECE IN A FATIGUE TEST

BACKGROUND OF THE INVENTION

This invention relates to a device for detecting the length of cracks of a fatigue test piece.

As a method of finding the bahavior of fracture of a component part, there has heretofore been developed a "K" value control device for displaying the speed of development of cracks of the component part due to its fatigue in terms of a stress intensity factor ("K" value) and controlling the load imposed thereon based on the factor or "K" value.

This control device is a fatigue test apparatus arranged to follow after the cracked leading end of a fatigued test piece such as flat metal sheet etc. by means of a chasing detector means, compute "K" value corresponding to the length of the crack and apply the resulting value of load on the test piece.

A hypothesis has been advocated in which the development of cracks in a component part is caused by a local stress exerted in the leading end of the crack and is determined thereby in principle. Stating in concrete manner, a stress intensity factor ("K" value) is given which is determined by the shape of the test piece, the load applied thereon and the length of the crack.

According to the hypothesis, if the amplitude of $\Delta K$ given by a fluctuation of the load is kept constant, then there is obtained a relationship between the stress intensity factor ("K" value) and the length of the crack "a" in which the speed of development or propagation of the crack $da/dN$ is kept constant, where "N" is the number of repetitions of application of the fluctuating load.

The following formula is given for example to calculate the tensile load.

$$P(\lambda) = twk/\sqrt{a}(1 + 0.5948\lambda^2 + 0.4812\lambda^4 + 0.3963\lambda^6 + 0.3238\lambda^8)$$

where
$\lambda = 2a/w$,
$t$ = thickness of plate,
$w$ = width of plate,
$2a$ = length of crack,
$k$ = stress intensity factor,
$P(\lambda)$ = tensile load.

Further, the "K" value control device is required to have such capacities as being capable of detecting the end of the crack and taking or reading out the location thereof as a signal, computing the load corresponding to a spontaneous value of $\Delta K$ based on the length of the crack and the shape of the test piece and applying the indicated load on the test piece.

SUMMARY OF THE INVENTION

It is therefore an object of the present invention to provide an apparatus for detecting crack length of a test piece in a fatigue test which is able to detect and measure crack length precisely.

Another object of the present invention is to provide an apparatus for detecting crack length of a test piece in a fatigue test wherein an image of the crack can be monitored on a monitor screen while detecting the length thereof.

A still further object of the present invention is to provide an apparatus for detecting crack length of a test piece in a fatigue test which can provide a high resolution image of the crack.

In accordance with an aspect of the present invention, there is provided an apparatus for detecting crack length of a test piece in a fatigue test:

comprising a light source;

irradiation means for irradiating the crack formed in the test piece by reflecting a light beam from said light source;

camera tube means for displaying an image of the crack thereon by means of reflected light beam from said test piece, said reflected light beam being adapted to pass through said irradiation means before reaching said camera tube means;

memory means for memorizing said image for an extended period;

monitor means connected to said memory means for monitoring said image of the crack;

image analyser means connected to said memory means for analyzing said image of the crack from signals supplied from said memory means, said image analyser means being also adapted to memorize data concerning positions of one of the leading ends of said crack when said leading end is adjusted to locate at a preset position on said monitor means;

transfer means for moving said irradiation means three dimensionally according to output signals from said image analyser means;

fatigue tester means for applying repeating loads on said test piece, said fatigue tester means being connected with said image analyser means and controlled thereby; and command controller means for controlling an overall time sequence of the apparatus based on load signals fed from said fatigue tester means.

The above and other objects, features and advantages of the present invention will be readily apparent from the following description taken in conjunction with the accompanying drawings.

BRIEF DESCRIPTION OF THE DRAWINGS

FIG. 3 is a time chart showing time sequence of various ous signals sent out from a command controller.

DETAILED DESCRIPTION OF THE INVENTION

Figure 1:
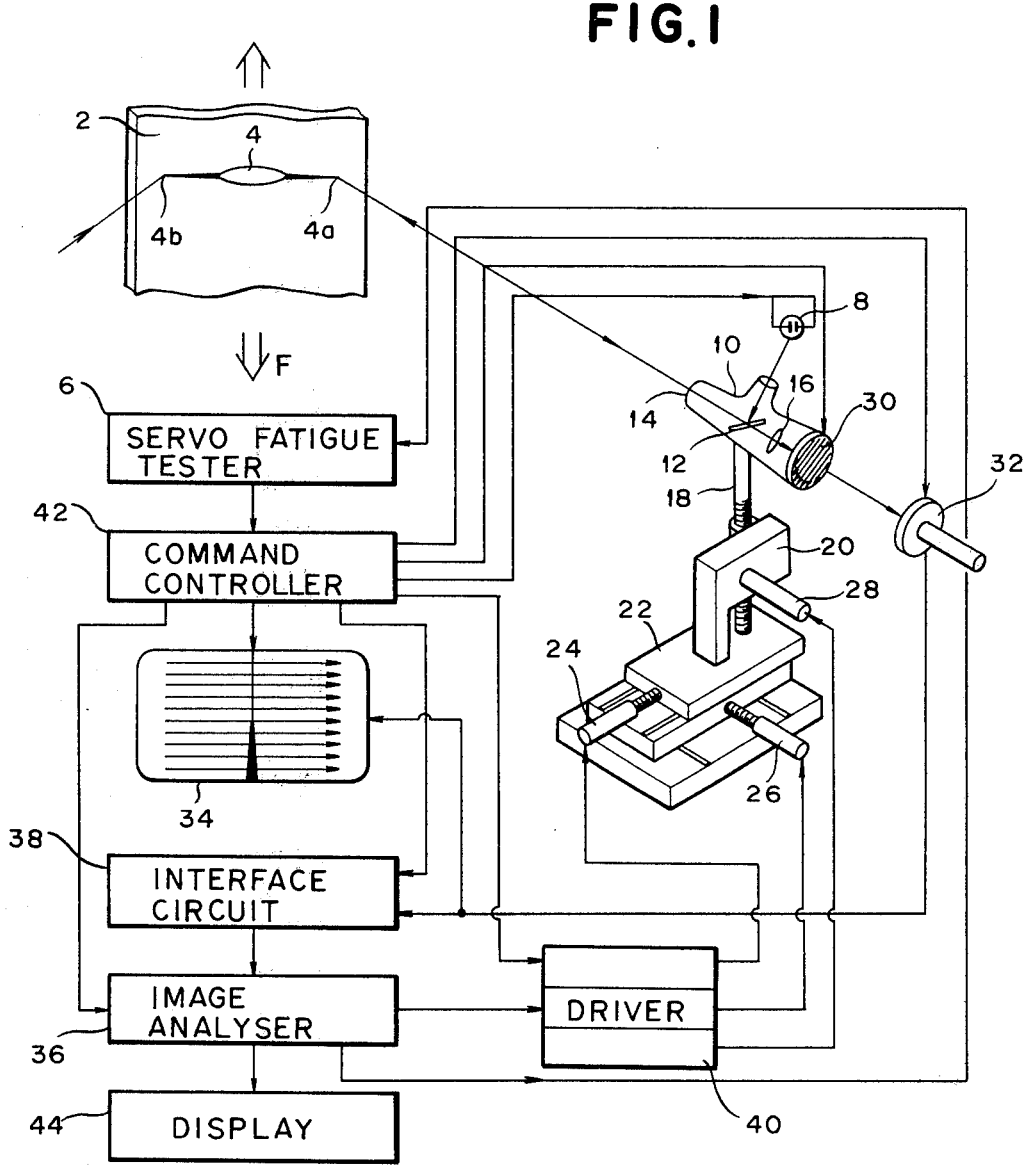
FIG. 1 is a schematical illustration of a crack detecting apparatus according to the present invention showing an entire arrangements thereof.

The present invention will now be described below by way of embodiment with reference to the accompanying drawings. A crack 4 formed in a fatigue test piece 2 is subjected to repeated load "F" by a servo fatigue tester so that it is alternately opened and closed, and leading ends 4a and 4b of the crack will develop gradually. In the crack 4, the light is not normally reflected, but transmitted or subjected to diffused reflection. Therefore, at the time of irradiation of light, the image forming face of the crack becomes dark in case of the regular reflection method, whilst the background becomes dark and the image forming face becomes bright in case of irregular reflection method.

Reference numeral 8 denotes a Strobo light source, and 10 an opticalscope in which a semi-reflection mirror 12 and lenses 14 and 16 are mounted. The opticalscope 10 is mounted on a support member 20 so that it can be moved up and down by means of a rod 18. The support member 20 is fixedly secured to a table 22. The table 22 can be moved in the directions of "X" axis and "Y" axis by the action of an "X" axis pulse motor 24 and a "Y" axis pulse motor 26, respectively. The opticalscope 10 can be moved up and down relative to the table 22 by the actuation of a "Z" axis pulse motor 28. Therefore, the opticalscope 10 can be moved in the three directions of "X" axis, "Y" axis and "Z" axis by driving the pulse motors 24, 26 and 28. Reference numeral 30 indicates a camera tube or image pick-up tube, which forms momentarily the image of the leading ends 4a or 4b of the crack by irradiating it with Strobo light. The image forming time of the camera tube 30 is equal to the flash time of the Strobo and is very short in the order of $10^{-6}$ second, and its afterimage is of 20 to 50 miliseconds. Therefore, the image obtained by the Strobo flash light is stored in a scanning converter memory 32 within such an afterimage forming time.

The storage or memory time of the scanning converter memory 32 is comparatively long in the order of 30 to 90 minutes. The stored image can be observed by using a monitor 34.

Reference numeral 36 denotes an image analyser comprises a mini-computer etc, and which is connected through an interface circuit 38 with the scanning converter memory 32. Reference numeral 40 indicates a driver which receives a signal from the image analyser 36, amplifies the signal and sends out output signals for driving the pulse motors 24, 26 and 28.

Reference numeral 42 denotes a command controller which comprises a mini-computer etc, and which receives a load signal from the servo fatigue tester 6 and sends out command signals to the Strobo light source 8, the camera tube 30, the scanning converter memory 32, the monitor 34, the interface circuit 38, the image analyser 36 and the driver 40.

Reference numeral 44 indicates a display means which displays the distance between the ends 4a and 4b of the crack which has been operated by the image analyser 36.

The operation of the device of the present invention will now be described below.

When the full load is applied on the test piece 2 and if a flash command signal is sent from the command controller 42 to the Strobo light source 8, the Strobo light is reflected by the semi-reflection mirror 12 and impinges on the test piece 2. The light which has been reflected by the surface of the test piece 2 will transmit straight through the lens 14, the semi-reflection mirror 12 and the lens 16 within the opticalscope 10 and form an image on the camera tube 30. At that time, as can be seen from the time chart shown in FIG. 3, a beam cut signal is sent from the command controller 42 to the camera tube 30 using as a trigger the off of "erase signal" sent from the command controller 42 to the scanning converter memory 32. The beam cut signal is used to make uniform the density of the image formed on the camera tube 30, and as can be seen from the time chart, it is sent to the camera tube 30 before the Strobo flash light signal is sent to it. The arrangement is made such that while the beam cut signal is being sent to the camera tube 30 the Strobo is rendered operative by the Strobo flash light signal. As aforementioned, since the image forming time of the camera tube 30 is very short, simultaneously with the beam cut signal being turned off, a "Write" signal is sent from the command controller 42 to the scanning converter memory 32 so that the image formed by the Strobo flash light can be stored in the scanning converter memory 32 within the afterimage forming time of the camera tube 30. Subsequently, a monitor display signal is sent from the command controller 42 to the monitor 34 so that the image stored or memorized in the scanning converter memory 32 can be observed by the monitor 34. Simultaneously with the transmission of the monitor display signal, an interface signal is sent from the command controller 42 to the interface circuit 38. Further, an image analyser signal is fed from the command controller 42 to the image analyser 36 using as a trigger the turning-off of the interface signal, and also the image signal stored in the scanning converter memory 32 is sent through the interface circuit 38 into the image analyser 36 where it is processed by its operation. Accordingly, the location of the end 4a of the crack 4 can be detected by the image analyser 36.

Simultaneously with the turning off of the image analyser signal, a drive signal is sent from the command controller 42 to the driver 40 so that, if the detected leading end of the crack is not located at a position designated by the monitor 34, then the driver 40 will transmit a signal which selectively drives the pulse motors 24, 26 and 28 and moves the opticalscope 10 through the table 22 thereby making controls to correspond the location of the leading end of the crack to the monitor's designated position.

When the position of the leading end 4a of the crack 4 has been registered with the monitor's designated location, data such as the applied load, number of repetitions of applying load and the position of the opticalscope 10 in the directions of X axis, Y axis and Z axis are stored in the image analyser 36. Subsequently, the opticalscope 10 is directed towards the other end 4b of the crack 4 by driving the pulse motor 24. By effecting the similar operation, the data of the end 4b of the crack 4 can be stored in the image analyser 36, and operation is made by the image analyser 36 based on the data of the ends 4a and 4b so as to send out a signal to the servo fatigue tester 2 thereby controlling the repeated load "F" applied to the test piece 2. The distance between both ends 4a and 4b of the crack 4 can be automatically read by the display means 44 by sending a signal produced by the result of operation made by the image analyser 36 to the display means. Strictly speaking, a time will lapse from the detection of the one end 4a of the crack 4 to that of the other end 4b thereof after the movement of the table 22, while the crack 4 will develop and therefore the accurate distance between the ends 4a and 4b cannot be obtained. However, the speed of development of the crack caused by applying repeated load for several hundred times is negligible, and so the distance between the ends 4a and 4b of the crack can be measured.

Figure 2:
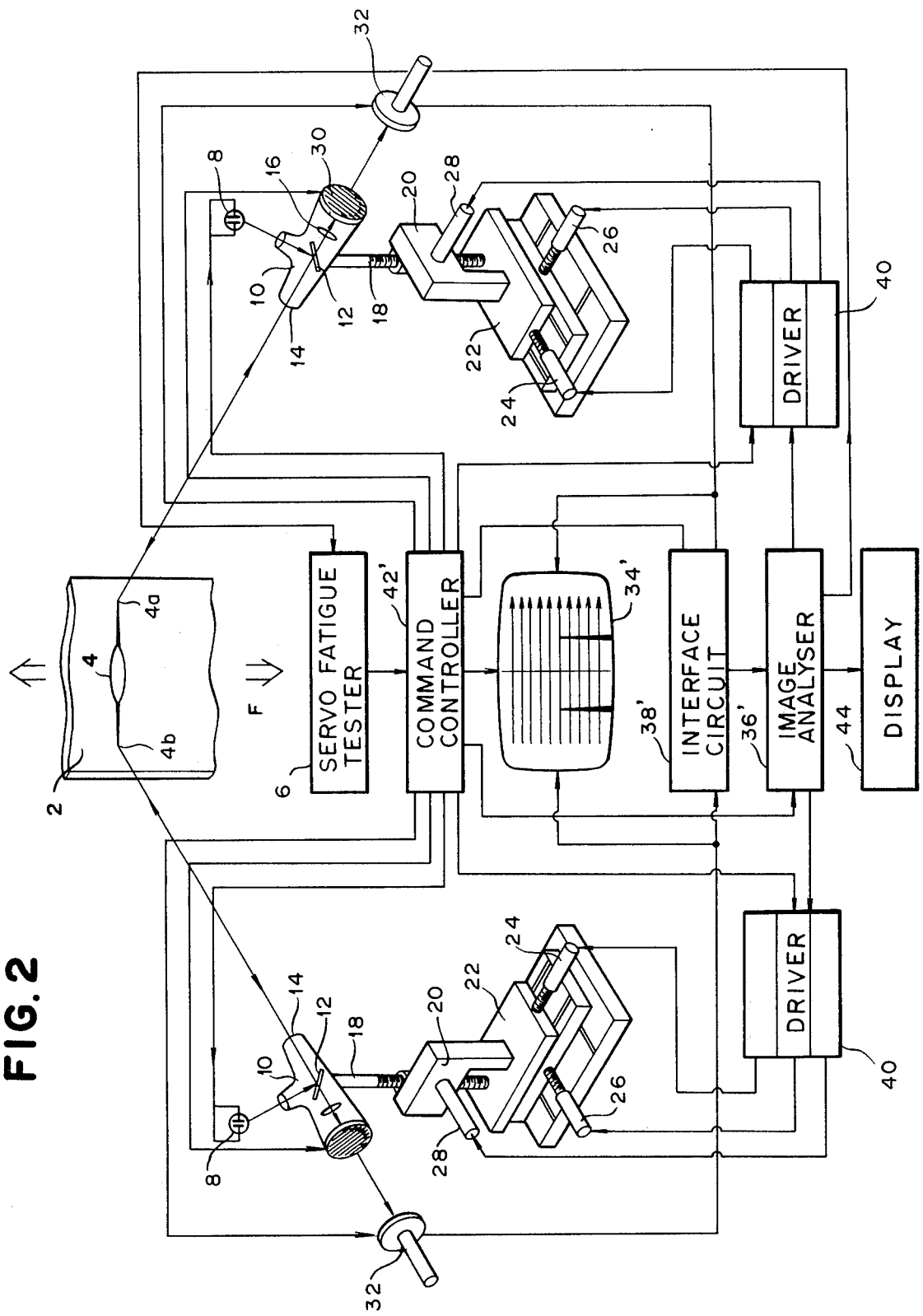
FIG. 2 is another embodiment of the present invention wherein both ends of a crack can be detected simultaneously.

Referring to FIG. 2 showing another embodiment of the present invention, there are provided a pair of Strobo light sources 8, opticalscopes 10, tables 22, scanning converter memorys 32 and drivers 40. The opticalscopes 10, 10 are directed towards the ends 4a and 4b of the crack 4, respectively, and by effecting the operation similar to that in the case of the aforementioned first embodiment, the crack ends 4a and 4b can be simultaneously observed on a monitor 34'. In this case, command controller 42', monitor 34', interface circuit 38' and image analyser 36' are required to modify more or less their parts corresponding to those of the first embodiment, but they are not much different from those of the first embodiment.

The apparatus according to this embodiment enables the ends 4a and 4b of the crack to be measured at the same time so that the distance between both ends can be accurately measured, but it is disadvantageous in that the size of the whole apparatus becomes larger thereby increasing the cost thereof.

While the invention has been described and shown with particular reference to the preferred embodiment, it will be apparent to those skilled in the art that variations and modifications might be possible that will fall within the scope of the present invention, which is not intended to be limited except as defined in the following claims.

What is claimed is:

1. An apparatus for detecting crack length of a test piece in a fatigue test:
    comprising a light source;
    irradiation means for irradiating the crack formed in the test piece by reflecting a light beam from said light source;
    camera tube means for displaying an image of the crack thereon by means of reflected light beam from said test piece, said reflected light beam being adapted to pass through said irradiation means before reaching said camera tube means;
    memory means for memorizing said image for an extended period;
    monitor means connected to said memory means for monitoring said image of the crack;
    image analyser means connected to said memory means for analyzing said image of the crack from signals supplied from said memory means, said image analyser means being also adapted to memorize data concerning positions of one of the leading ends of said crack when said leading end is adjusted to locate at a preset position on said monitor means;
    transfer means for moving said irradiation means three dimensionally according to output signals from said image analyser means;
    fatigue tester means for applying repeating loads on said test piece, said fatigue tester means being connected with said image analyser means and controlled thereby; and
    command controller means for controlling an overall time sequence of the apparatus based on load signals fed from said fatigue tester means;

2. An apparatus as defined in claim 1 wherein said light source is a Strobo light and said irradiation means is an opticalscope having a semi-transparent mirror mounted therein.

3. An apparatus as defined in claim 1 wherein said transfer means comprises a table, and a first, a second and a third pulse motors mounted on said table, said first, second and third pulse motors being arranged at right angles to each other.

4. An apparatus as defined in claim 1 or 3 further comprising driver means interposed between said image analyser means and said transfer means, said driver means being adapted to send out signals to each of said pulse motors based on signals supplied from said image analyser means.

5. An apparatus as defined in claim 1, 2 or 3 further comprising display means connected to said image analyser means for displaying a distance between both ends of said crack.

6. An apparatus for detecting crack length of a test piece in a fatigue test;
    comprising a pair of light sources;
    a pair of irradiation means for irradiating the crack formed in the test piece by reflecting light beams from said light sources;
    a pair of camera tube means each for displaying an image of the crack thereon by means of reflected light beam from said test piece, said reflected light beam being adapted to pass through said irradiation means before reaching said camera tube means;
    a pair of memory means for memorizing said image for an extended period;
    monitor means connected to each of said memory means for monitoring said image of the crack;
    image analyser means connected to said memory means for analying said image of the crack from signals supplied from said each memory means, said image analyser means being also adapted to memorize data concerning positions of both ends of said crack when said both ends are adjusted to locate at preset positions on said monitor means;
    a pair of transfer means for moving said irradiation means three dimensionally according to output signals from said image analyser means;
    fatique tester means for applying repeating loads on said test piece, said fatigue tester means being connected with said image analyser means and controlled thereby; and
    command controller means for controlling an overall time sequence of the apparatus based on load signals fed from said fatigue tester means.

7. An apparatus as defined in claim 6 wherein said light sources are Strobo lights and said irradiation means are opticalscopes each having a semi-transparent mirror mounted therein.

8. An apparatus as defined in claim 6 wherein each of said transfer means comprises a table, and a first, a second and a third pulse motors mounted on each of said tables, said first, second and third pulse motors being arranged at right angles to each other.

9. An apparatus as defined in 6 or 7 further comprising a pair of driver means each interposed between said image analyser means and each of said transfer means, said driver means being adapted to send out signals to each of said pulse motors based on signals supplied from said image analyser means.

10. An apparatus as defined in claim 6, 7 or 8 further comprising display means connected to said image analyser means for displaying a distance between both ends of said crack.

* * * * *